United States Patent [19]
Pystynen et al.

[11] Patent Number: 6,150,412
[45] Date of Patent: Nov. 21, 2000

[54] CATECHOL DERIVATIVES

[75] Inventors: Jarmo Pystynen, Espoo; Anne Luiro, Helsinki; Timo Lotta, Vantaa; Martti Ovaska, Espoo; Jukka Vidgren, Helsinki, all of Finland

[73] Assignee: Orion-yhtyma Oy, Espoo, Finland

[21] Appl. No.: 08/945,928

[22] PCT Filed: May 23, 1996

[86] PCT No.: PCT/FI96/00295

§ 371 Date: Nov. 21, 1997

§ 102(e) Date: Nov. 21, 1997

[87] PCT Pub. No.: WO96/37456

PCT Pub. Date: Nov. 28, 1996

[30] Foreign Application Priority Data

May 24, 1995 [GB] United Kingdom .................... 9510481

[51] Int. Cl.[7] .......................... A61K 31/192; A61P 9/12; A61P 25/16; C07C 229/42
[52] U.S. Cl. .......................... 514/568; 514/381; 514/557; 514/570; 514/646; 514/741; 548/250; 558/411; 558/412; 562/458; 562/409; 562/473; 562/474; 562/475
[58] Field of Search ...................... 514/557, 568, 514/570, 646, 741, 381; 548/250; 558/411, 412; 562/458, 409, 473, 474, 475

[56] References Cited

U.S. PATENT DOCUMENTS

| 4,707,488 | 11/1987 | Kaiser et al. | 514/381 |
|---|---|---|---|
| 5,191,108 | 3/1993 | Carson et al. | 560/64 |
| 5,389,653 | 2/1995 | Bernauer et al. | 514/355 |

FOREIGN PATENT DOCUMENTS

| 2607493 | 6/1988 | France . |
|---|---|---|
| 2200109 | 7/1988 | United Kingdom . |

OTHER PUBLICATIONS

Bhatt M. V. and Kulkarni S. U., "Cleavage of Ethers", Synthesis, 1983, 249–282, Georg Thieme Verlag.

Bäckström R. et al., "Synthesis of Some Novel Potent and Selective Catechol O–Methyltransferase Inhibitors", J. Med. Chem., 1989, 32, 841–846.

Pérez R. A. et al., "Inhibition of Catechol–O–methyltransferase by 1–Vinyl Derivatives of Nitrocatechols and Nitroguaiacols", Biochemical Pharmacology, 1993, 45(10), 1973–1981.

Eklöf A.–C. et al., "Natriuretic and Vasodilating Effects of Dopamine Are Mimicked by Oral Administration of a Catechol–O–methyltransferase (COMT) Inhibitor", J. Am. Soc. Nephrology, 1994, 5(3), 657.

Primary Examiner—Joseph McKane
Assistant Examiner—Jane C. Osowecki
Attorney, Agent, or Firm—Finnegan, Henderson, Farabow, Garrett & Dunner, L.L.P.

[57] ABSTRACT

The invention relates to compounds of formula (I)

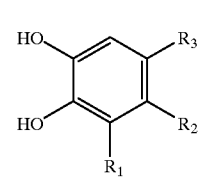

wherein $R_1$ is an electronegative substituent, preferably nitro, cyano, formyl or carboxy, $R_2$ is —A—$R_4$, wherein A is a branched or straight chain $C_{1-9}$ alkylene and $R_4$ is carboxy or 5-tetrazolyl; $R_3$ is an electronegative substituent, preferably nitro, cyano, halogen, formyl, carboxy, $C_{1-5}$ alkyl carbonyl, aryl carbonyl or $SO_2R_6$, wherein $R_6$ is a branched or straight chain $C_{1-5}$ alkyl, aryl alkyl, aryl or $NR_7R_8$, wherein $R_7$ and $R_8$ are independently hydrogen, a branched or straight chain $C_{1-5}$ alkyl or together form a $C_{3-6}$ ring; or a pharmaceutically acceptable ester or salt thereof. The compounds are peripheral, long acting COMT (catechol-O-methyl transferase) inhibitors and are useful, e.g., in the treatment of Parkinson's disease and hypertension.

9 Claims, No Drawings

CATECHOL DERIVATIVES

This application is a 371 of PCT/FI96/00295 filed May 23, 1996.

The present invention relates to new trisubstituted catechol derivatives, to their preparation and use, to pharmaceutically acceptable esters and salts thereof and to pharmaceutical compositions containing them.

The compounds of the present invention are very potent peripheral, long acting COMT (catechol-O-methyl transferase) inhibitors. The main use of COMT-inhibitors lies presently in the potentiation of levodopa therapy which is used to treat Parkinson's disease. However, many other uses have been suggested including use as natriuretic and antihypertensive agents (Eklöf A. C., et al. Natriuretic and vasodilating effects of dopamine are mimicked by oral administration of a catechol-O-methyltransferase (COMT) inhibitor, J. Am. Soc. Nephrology Vol. 5, No. 3, p. 657).

GB-A-2200109 discloses disubstituted catechols of formula:

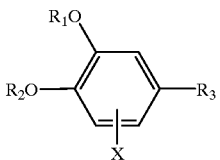

wherein $R_1$ and $R_2$ represent different substituents including hydrogen, X comprises an electronegative substituent such as halogen, nitro, cyano, lower alkyl sulfonyl, sulfonamido, trifluoromethyl, aldehyde or carboxyl and $R_3$ can be, inter alia, carboxyalkyl or substituted vinyl (comparison compounds 1 and 2 fall within this formula). These compounds are COMT inhibitors. Disubstituted catechols having 2-(3, 4-dihydroxy-2-nitrophenyl)vinyl structure disclosed by Perez et al in Biochemical Pharmacology, Vol. 45 (1993) No. 10 pp. 1973–1981 are also reported to be COMT-inhibitors.

The compound of the present invention are of formula I:

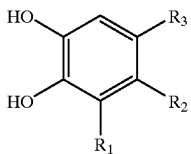

wherein $R_1$ is an electronegative substituent, preferably nitro, cyano a formyl or carboxy
  $R_2$ is —A—$R_4$, wherein
    A is branched or straight chain $C_{1-9}$ alkylene and
    $R_4$ is carboxy or 5-tetrazolyl, $R_5$ or CO-$R_5$, wherein
    $R_5$ is phenyl or $C_{3-7}$ cycloalkyl which is substituted by at least one carboxy or 5-tetrazolyl;
  $R_3$ is an electronegative substituent, preferably nitro, cyano, halogen, formyl, carboxy, $C_{1-5}$ alkyl carbonyl, aryl carbonyl or $SO_2R_6$ wherein
    $R_6$ is branched or straight chain $C_{1-5}$ alkyl, aryl alkyl, aryl or $NR_7R_8$, wherein
    $R_7$ and $R_8$ are independently hydrogen or branched or straight chain $C_{1-5}$ alkyl or together form a $C_{3-6}$ ring or a pharmaceutically acceptable ester or salt thereof.

The term "aryl" as employed herein means phenyl or naphthyl.

Preferably $R_1$ and $R_3$ are both nitro or cyano and A has at least 2 carbon atoms.

Preferred salts are metal or amine salts. More preferred are alkaline metal salts such as the sodium salt.

The compounds of the invention may be prepared by dealkylating a compound of formula II

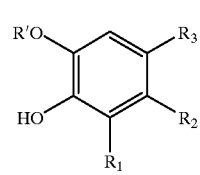

wherein $R^1$ is a lower alkyl or benzyl and $R_1$ to $R_3$ are as defined above to form a compound of formula I. The dealkylation may be carried out by usual dealkylation procedures described in the literature (See, Cleavage of Ethers, Bhatt, M. V., Synthesis 1983, page 249), for example, using boron tribromide at a temperature ranging from −20° C. to 40° C. under an inert atmosphere or using pyridine hydrochloride at a temperature between 180° C. and 225° C.

The starting materials may be prepared by any method known for the preparation of analogous compounds.

Compounds of formula I wherein $R_1$ and $R_3$ are both nitro or formyl are typically prepared by first disubstituting a compound of formula III

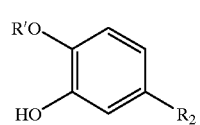

wherein R' and $R_2$ are the same as above to obtain the intermediate of formula II wherein $R_1$ and $R_3$ are both nitro or formyl which intermediate is then demethylated to form the desired compound.

The dinitro intermediates of formula II may be prepared by any procedure known in the art, for instance, by using nitric acid in acetic acid at temperatures ranging from 20° C. to 80° C., by using nitric acid in dichloromethane between 0° C. to 40° C. or by using potassium nitrate in sulfuric acid at temperatures from −15° C. to 20° C. The corresponding diformyl compounds may be prepared by common electrophilic formylation procedures, preferably by the Duff reaction using hexamethylenetetramine in acetic or trifluoroacetic acid.

The intermediates of formula II wherein $R_1$ and $R_3$ are both cyano may be prepared from the compounds of formula III wherein $R_1$ and $R_3$ are both formyl in a known manner, for example, by refluxing them in a mixture of hydroxylamine hydrochloride, (sodium formate) and formic acid. The corresponding compounds of formula II wherein $R_1$ and $R_3$ are both carboxy may be prepared by hydrolysis from the compound of formula II wherein $R_1$ and $R_3$ are both cyano or by oxidation from the compound of formula II wherein $R_1$ and $R_3$ are both formyl.

In another method a compound of formula IV

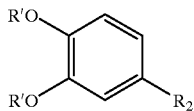

wherein R' and R$_2$ are as defined above is monosubstituted to give a compound of formula V

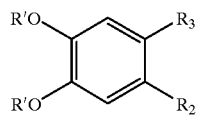

wherein R', R$_2$ and R$_3$ are as defined above. Any known electrophilic aromatic substitution reaction may be used. For instance, it is possible to carry out the well known Friedel-Crafts-reaction using acid chloride or sulfonylchloride in presence of a Lewis-catalyst to obtain the compounds of formula V wherein R$_3$ is alkyl, aryl carbonyl or SO$_2$R$_6$. Compounds wherein R$_3$ is nitro may be obtained using nitric acid in the same manner as described above and compounds wherein R$_3$ is formyl, cyano or carboxy may be obtained by formylation and subsequent transformation as described above. Finally, it is possible to obtain compounds of formula V wherein R$_3$ is halogen by halogenating in a known manner.

Thereafter the compound of formula V is selectively dealkylated to give the compound of formula VI

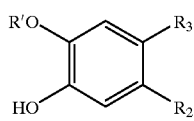

wherein R', R$_2$ and R$_3$ are as defined above. The selective dealkylation may be accomplished using any method known in the literature, for example, using the sodium salt of thiophenol in DMF at temperatures ranging from 100° C. to 150° C.

The compound of formula VI is then substituted for a second time as described above to give an intermediate of formula II which is finally dealkylated as described above to give a compound of the invention.

The compounds of the invention are preferably administered enterally but may also be administered topically or parenterally. Accordingly, they may be formulated alone or together with one or more other active ingredients to different pharmaceutical unit dosage forms i.e. tablets, capsules, solutions, emulsions and powders etc. using conventional techniques. The pharmaceutical carriers employed are selected with the planned manner of administration in mind. Generally, the active ingredient is dispensed in unit form comprising 0.05–100 mg in a pharmaceutically acceptable carrier per unit dosage, depending on the type of the dosage form.

The appropriate oral dosage for the compounds of the invention depends on several factors such as the age and the sex of the patient, the severity of the condition to be treated and on the method of administration. Accordingly, suitable oral dosage ranges are typically 1–200 mg daily, depending upon the form in which the compound is administered, the indication towards which the administration is directed, the subject involved and the body weight of the subject involved.

The invention also provides a compound of the invention or an ester or salt thereof for use in a method of treatment of the human or animal body.

The present invention further provides a compound of the invention or an ester or salt thereof for use in the treatment of Parkinson's disease or hypertension.

The invention also provides the use of a compound of the invention or an ester or salt thereof in the manufacture of a medicament for the treatment of Parkinson's disease or hypertension.

The invention further relates to a method for the treatment of Parkinson's disease or hypertension by administering to a subject in need of such treatment an effective amount of a compound of the invention or an ester or a salt thereof.

Test Results

Determination of IC$_{50}$ Values

The studied inhibitors were first dissolved into 0.1 M NaOH solution and then diluted with distilled water to 0.5 mM inhibitor concentration. From this stock solution the inhibitor concentrations were adjusted by diluting the desired amounts of stock solution with 0.05 M phosphate buffer, pH 7.4. The studied sample solutions were prepared into the Eppendorf tubes. The final concentrations of the studied samples were; ~100 mM phosphate buffer, 5 mM MgCl$_2$, 0.05 mM AdoMet, S-COMT enzyme (about 30 nM) and the inhibitor. The final inhibitor concentration for an IC$_{50}$ determination varied from 0 to 1000 nM.

The samples were mixed with Vortex, and incubated for 5 min at 37° C. The reactions were initiated with 3 mM dopamine and carried on for 15 min at 37° C. The reactions were stopped with 4 M perchloric acid and stabilized afterwards for 10 min in ice bath. The sample solutions were centrifuged for 10 min, and the methylated products, 3-methyldopamine and 4-methyldopamine, were analysed with HPLC. The results were calibrated with 3-methyldopamine standards.

Determination of plasma concentrations

Male Wistar rats (220–280 g) were orally dosed (10 mg/kg) with test compounds. Control animals received the vehicle only. Blood samples were drawn from the tail artery 0.5 and 5 hours after the treatment and collected into pre-cooled Li-heparinized tubes. The plasma was separated by centrifugation (11000 g, 5 min) and stored at −80° C. until analysis.

The analytes were extracted from 200 μl of acidified plasma (100 μl of 1 M HCl) with 5 ml of ethyl acetate. The organic phase (4 ml) was evaporated to dryness under a stream of nitrogen at 40° C. The residue was redissolved in 200 μl of dimethylsulphoxide and 30 μl of it was analyzed by HPLC with amperometric detection. The electrode potential was +700 mV.

The test results are given in Table 1.

TABLE 1

IC$_{50}$ values and plasma concentrations

| Compound of the example | IC$_{50}$ (nM) | Plasma c (ng/ml) t = 30 min | Plasma c (ng/ml) t = 5 h |
| --- | --- | --- | --- |
| 15 | 60 | | |
| 11 | 30 | 2100 | 490 |
| 14 | 30 | | |
| 13 | 20 | | |
| 17 | 20 | | |
| 16 | 15 | 2000 | 150 |
| Comparison compound 1 | 90 | | |
| Comparison compound 2 | 20 | 530 | <25 |

Comparison compound 1: 5-(3,4-Dihydroxy-5-nitrophenyl) pentanoic acid
Comparison compound 2: Nitecapone (2[(3,4-dihydroxy-5-nitrophenyl)methylene]-2,4-pentanedione)

The following examples illustrate how compounds of the invention may be prepared.

EXAMPLE 1

4-(5-HYDROXY-4-METHOXY-2-NITROPHENYL)BUTANOIC ACID

Fuming nitric acid (1.4 ml) was added to a solution of 4-(3,4-dimethophenyl)butanoic acid (7.8 g) in acetic acid (25 ml) at room temperature and the mixture was stirred for fifteen minutes. The product crystallized and was filtered. Yield: 6.4 g of 4-(4,5-dimethoxy-2-nitrophenyl)butanoic acid. $^1$H-NMR (DMSO-d$_6$, 400 MHz): 1.79–1,84 (m, 2H), 2.25–2.29 (m, 2H), 2.84–2.86 (m, 2H), 3.83 (s, 3H), 3.89 (s, 3H), 7.01 (s, 1H), 7.56 (s, 1H), 12.07 (s, 1H).

To a solution of 4-(4,5-dimethoxy-2-nitrophenyl)butanoic acid (4.75 g) and thiophenol (2 g) in N,N-dimethylformamide (40 ml) was added NaH dispersion (1.1 g, 80% NaH in mineral oil). The mixture was stirred under nitrogen at 140–150° C. for three hours, poured into cold water and acidified. The solid was filtered, washed with water and dried under vacuum. Finally, the product was triturated with diethyl ether. Yield: 3.37 g.

$^1$H-NMR (DMSO-d$_6$, 400 MHz): 1.75–1.79 (m,2H), 2.25 (t, 2H, J=8 Hz), 2.80 (t, 2H, J=8 Hz), 3.84 (s,3H), 6.79 (s,1H), 7.59 (s, 1H), 10,51 (s, 1H,), 12.07 (s, 1H,).

EXAMPLE 2

4-(2,6-DINITRO-3-HYDROXY-4-METHOXYPHENYL)BUTANOIC ACID

The product from Example 1 (0.77 g) was dissolved in concentrated sulfuric acid and cooled to −15° C. Potassium nitrate (0.31 g) was gradually added to this solution while maintaining the reaction temperature between −15 and −10° C. The resultant mixture was stirred at −15° C. for half an hour and then poured into ice. The solid was washed with water and dried.

Yield: 0.54 g, melting point 168–175° C.; $^1$H-NMR (DMSO-d$_6$, 400 MHz): 1.72–1.78 (m, 2H), 2.25 (t, 2H, J=8 Hz), 2.67 (m, 2H), 3.97 (s, 3H, ),7.82 (s, 1H, ArH), 9–12 (br, 2H,).

EXAMPLE 3

2,6-DINITRO-3-HYDROXY-4-METHOXYPHENYLACETIC ACID

To a slurry of 3-hydroxy-4-methoxyphenylacetic acid (1.66 g) in acetic acid (10 ml) was gradually added nitric acid in acetic acid (9.6 ml of 2 M solution) and the resulting solution was stirred at room temperature for half an hour. The separated crystals were filtered and recrystallized from acetic acid.

Yield: 0.57 g, melting point 196–198° C.; $^1$H-NMR (DMSO-d$_6$, 400 MHz): 3.71 (s, 2H,), 3.98 (s, 3H,), 7.88 (s, 1H), 11–13 (b, 2H).

EXAMPLE 4

3-(2,6-DINITRO-3-HYDROXY-4-METHOXYPHENYL)PROPIONIC ACID

Using the procedure described in Example 3, 3-(3-Hydroxy-4-methoxyphenyl)propionic acid (7.7 g) was converted to 3-(2,6-dinitro-3-hydroxy-4-methoxyphenyl) propionic acid. Yield: 5.4 g, melting point 195° C.

$^1$H-NMR (DMSO-d$_6$, 400 MHz): 2.49 (t, 2H, J=8 Hz), 2.86 (t, 2H, J=8 Hz), 3.97 (s, 3H), 7.83 (s, 1H), 11.8–12.2 (br, 2H,).

EXAMPLE 5

5-(2,6-DINITRO-3-HYDROXY-4-METHOXYPHENYL)-PENTANOIC ACID 5-(3-Hydroxy-4-methoxyphenyl)pentanoic acid (2 g) was suspended in ether (25 ml) and a solution of nitric acid in dichloromethane (2 M, 9.4 ml) was gradually added at 0–5° C. The resultant mixture was refluxed for one hour. The solution was decanted from the separated brown oil, evaporated and the resultant semicrystalline solid recrystallized twice from acetic acid. Yield: 0.56 g, melting point 168–170° C.

$^1$H-NMR (DMSO-d$_6$, 400 MHz): 1.50–1.55 (m, 4H), 2.21(t, 2H, J=8 Hz), 2.63 (t, 2H, J=8 Hz), 3.96 (s, 3H), 7.81 (s,1H), 12 (br, 2H).

EXAMPLE 6

5-(2,6-DIFORMYL-3-HYDROXY-4-METHOXYPHENYL)PENTANOIC ACID 5-(3-Hydroxy-4-methoxyphenyl)pentanoic acid (8 g) and hexamethylenetetramine (10 g) in acetic acid (150 ml) were heated under reflux over night. 70 ml 6 M Hydrochloric acid was added to the reaction mixture and it was refluxed for half an hour. The mixture was poured into water and extracted with dichloromethane. The organic phase was evaporated in vacuo and the residue triturated with diethyl ether. Yield 3.04 g.

$^1$H-NMR (DMSO-d$_6$, 400 MHz): 1.49–1.64(m, 4H), 2.23–2.26(m, 2H), 3.29–3.33(m, 2H), 3.88 (s, 3H), 7.57 (s, 1H), 10.24 (s, 1H), 10.46 (s, 1H), 12.01 (s, 1H).

EXAMPLE 7

3-(2,6-DIFORMYL-3-HYDROXY-4-METHOXYPHENYL)PROPANOIC ACID

The title compound was prepared from 3-(3-hydroxy-4-methoxyphenyl)propanoic acid (0.3 g) by the method of Example 6. Yield 0.33 g mp. 164–166° C.

$^1$H NMR (DMSO-d6, 400 MHz): 2.50–2.53(m, 2H), 3.41–3.51 (m, 2H), 3.89 (s, 3H), 7.59 (s, 1H), 10.10 (s, 1H), 10.47 (s, 1H), 11.88 (s, 1H), 12.2 (br, 1H).

EXAMPLE 8

5-(2,6-DICYANO-3-HYDROXY-4-METHOXYPHENYL)PENTANOIC ACID 5-(2,6-Diformyl-3-hydroxy-4-methoxyphenyl)pentanoic acid (3.0 g), hydroxylamine hydrochloride (1.8 g), sodium formate (2.3 g) and formic acid (15 ml) were heated under reflux for 2 h. The mixture was poured into water, extracted with ethyl acetate and the organic phase evaporated in vacuo. Yield 2.2 g.

$^1$H NMR (DMSO-d6, 400 MHz): 1.53–1.62(m, 4H), 2.23–2.25(m, 2H) 2.80–2.81(m, 2H), 3.88 (s, 3H), 7.61 (s, 1H), 11,5–12.4 (br, 2H).

EXAMPLE 9

3-(2,6-DICYANO-3-HYDROXY-4-METHOXYPHENYL)PROPANOIC ACID

The title compound was prepared from the product of Example 7 (0.7 g) by the method of Example 8. Yield 0.35 g $^1$H NMR (DMSO-d6, 400 MHz): 2.56 (t, 2H, J=8Hz), 3.04 (t, 2H, J=8Hz), 3.89 (s, 3H), 7.63 (s, 1H), 11.7–12.4 (br, 2H).

EXAMPLE 10

3,4-DIHYDROXY-2,6-DINITROPHENYLACETIC ACID

The product from Example 3 (0.28 g) 3 was slurried in dichoromethane (15 ml), cooled to –20° C. and boron tribromide (0.4 ml) added under nitrogen. The reaction mixture was allowed to warm up to room temperature and then refluxed for four hours. The mixture was poured into ice-water and extracted to ethyl acetate. The product was purified by column chromatography using toluene-ethyl acetate-acetic acid 8:1:1 as the eluent. Yield: 21 mg, melting point 178–184° C.

$^1$H-NMR (DMSO-d$_6$, 400 MHz): 3.79 (s,2H), 7.71 (s, 1H), 10–11 (b, 1H), 12.4 (br, 1H).

EXAMPLE 11

3-(3,4-DIHYDROXY-2,6-DINITROPHENYL)-PROPANOIC ACID

The product from Example 4 (2.0 g) was slurried in dichloromethane (100 ml) under nitrogen, cooled to –20° C. and boron tribromide (1.3 ml) added. The resultant mixture was stirred at –20° C. for half an hour and then at room temperature overnight. The mixture was poured into ice water, extracted in ethyl acetate and evaporated. The product was recrystallized from acetic acid.Yield: 0,6 g, melting point 162–165° C.

$^1$H-NMR (DMSO-d$_6$, 400 MHz): 2.47 (t, 2H, J=8 Hz), 2.85 (t,2H, J=8 Hz), 7.67 (s, 1H), 10.4–12.2 (br,3H).

EXAMPLE 12

4-(3,4-DIHYDROXY-2,6-DINITROPHENYL)-BUTANOIC ACID

The product from example 2 (0.5 g) was demethylated with boron tribromide according to the procedure described in example 10. Yield: 90 mg, melting point 165–170° C.

$^1$H-NMR (DMSO-d$_6$, 400 MHz): 1.72–1.78 (m, 2H), 2.22–2.26 (m, 2H), 2.63–2.67 (m, 2H), 7.65 (s, 1H), 11.3–11.5 (b, 1H), 12.1–12.2 (br, 1H).

EXAMPLE 13

5-(3,4-DIHYDROXY-2,6-DINITROPHENYL)-PENTANOIC ACID

The product from example 5 (0.5 g) was reacted with boron tribromide according to the procedure described in example 10. Yield: 0.13 g, melting point 135–139° C.

$^1$H-NMR (DMSO-d$_6$, 400 MHz): 1.50–1.54 (m, 4H), 2.19–2.22 (m, 2H), 2.62 (t, H, J=8Hz), 7.63 (s, 1H), 11–13 (br, 3H).

EXAMPLE 14

5-(2.6-DIFORMYL-3,4-DIHYDROXYPHENYL) PENTANOIC ACID

The title compound was prepared from the product of Example 6 (0.4 g) by the method of Example 11. Yield 0.16 g mp. 148–152° C.

$^1$H NMR (DMSO-d6, 400 MHz):1.52–1.64 (m, 4H), 2.24 (t, 2H, J=8Hz), 3.28 (t, 2H, J=8Hz), 7.47 (s, 1H), 10.05 (s, 1H), 10.19 (s, 1H), 10.44 (s, 1H) 11.92 (s, 2H).

EXAMPLE 15

3-(2,6-DIFORMYL-3,4-DIHYDROXYPHENYL) PROPANOIC ACID

The title compound was prepared from the product of Example 7 (0.3 g) by the method of Example 10. Yield 0.07 g mp. 160–162° C.

$^1$H NMR (DMSO-d6, 400 MHz):2.49–2.52 (m, 2H), 3.47 (t, 2H, J=8HZ), 7.45 (s, 1H), 10.16 (s, 1H), 10.45 (s, 1H), 10.5–12.5(br, 3H).

EXAMPLE 16

5-(3,4-DIHYDROXY-2,6-DICYANOPHENYL) PENTANOIC ACID

The title compound was prepared from the product of Example 8 (0.56 g) by the method of Example 11. The product was recrystallized from acetic acid. Yield 0.10 g mp. 210–215° C.

$^1$H NMR (DMSO-d6, 400 MHz):1.51–1.60(m,4H), 2.23–2.26(m, 2H), 2.76–2.80(m, 2H), 7.23 (s, 1H), 10.5–12.2 (br, 3H).

EXAMPLE 17

3-(2,6-DICYANO-3,4-DIHYDROXYPHENYL) PROPANOIC ACID

The title compound was prepared from the product of Example 9 (0.32 g) by the method of Example 10. Yield 0.10 g mp. 210–220° C.

$^1$H NMR (DMSO-d6, 400 MHz):2.50–2.55(m,2H), 3.0(t, 2H, J=8Hz), 7.19 (s, 1H), 10.4–12.5 (br, 3H)

EXAMPLE 18

3-(3,4-DIHYDROXY-2,6-DINITROPHENYL) PROPANOIC ACID

Pyridine (16 ml) and concentrated hydrochloride acid (16.6 ml) were heated at 150° C. until the evaporation of water was ceased. 3-(2,6-Dinitro-3-hydroxy-4-methoxyphenyl)propanoic acid (2.3 g) was added and the resulting mixture heated at reflux for two minutes. The product mixture was cooled to about 150° C. and poured to ice water. The mixture was extracted with ethyl acetate and the product finally recrystallized from acetic acid. Yield: 0.93 g, melting point 165–166° C. NMR-data identical to that of example 11.

EXAMPLE 19

6-(4,5-DIMETHOXY-2-NITROPHENYL) HEXANOIC ACID.

To a solution of 6-(3,4-dimethoxyphenyl)hexanoic acid (2.7 g) in acetic acid (10 ml) was added nitric acid (5.4 ml of a 2 M solution in acetic acid) and the mixture stirred at room temperature for one hour. The mixture was evaporated and the product used as such for the next step. Yield: 3.2 g.

$^1$H-NMR (DMSO-d6, 400 MHz): 1.32–1.36 (m, 2H), 1.51–1.55 (m, 4 H), 2.19–2.23 (m, 2H), 2.80–2.84 (m, 2H), 3.81 (s, 3H), 3.88 (s, 3H), 7.02 (s, 1H), 7.54 (s,1H), 12.0 (br, 1H).

EXAMPLE 20

6-(5-HYDROXY-4-METHOXY-2-NITROPHENYL)HEXANOIC ACID

The product from the previous example (3.2 g) was demethylated using the procedure described in example 1. The product was purified by column chromatography using toluene-ethyl acetate-acetic acid 8:1:1 as the eluent:

Yield: 1.6 g.; $^1$H-NMR (DMSO-d6, 400 MHz): 1.32–1.34 (m, 2H), 1.52–1.54 (m, 4H), 2.18–2.22 (m, 2H), 2.75–2.78 (m, 2H), 3.83 (s, 3H), 6.78 (s, 1H), 7.57 (s,1H), 10–10.8 (br, 1H), 11.8–12.2 (br, 1H).

EXAMPLE 21

6-(2,6-DINITRO-3-HYDROXY-4-METHOXYPHENYL)HEXANOIC ACID

To the solution of the product from the previous example (0.6 g) in acetic acid (5 ml) was added fuming nitric acid (0.1 ml). The solution was kept at room temperature overnight and then poured into ice water. The product was extracted in ether and evaporated. It was used as such in the following step.Yield; 0.45 g.

$^1$H-NMR (DMSO-d6, 400 MHz): 1.30–1.32 (m, 2 H), 1.46–1.51 (m, 4 H), 2.18–2.21 (m, 2 H), 2.5–2.6 (m,2 H), 3.96 (s, 3H), 7.82 (s,1H), 10.5–12.5 (br, 2H).

EXAMPLE 22

6-(3,4-DIHYDROXY-2,6-DINITROPHENYL) HEXANOIC ACID

The product from the previous example was demethylated with pyridine hydrochloride as described in example 18. The product was purified by column chromatography using toluene-ethyl acetate-acetic acid 8:1:1 as the eluent and recrystallized from water. Yield: 18 mg. Mp. 120–127° C.

$^1$H-NMR (DMSO-d6, 400 MHz): 1.30–1.32 (m, 2H), 1.46–1.52 (m, 4H), 2.17–2.21 (m, 2H), 2.58–2.62 (m, 2H), 7.63 (s, 1H), 9.5–10.8 (br, 1H), 11 (br, 1H), 12 (br,1H).

EXAMPLE 23

4-(2-FORMYL-3-HYDROXY-4-METHOXY-6-NITROPHENYL)BUTANOIC ACID.

The title compound was prepared from the product of example 1 (0.5 g) by the method of example 6. The product was used for the next step without any purification. Yield: 0.2 g $^1$H-NMR (DMSO-d6, 400 MHz): 1.77–1.80 (m, 2H), 2.31 (t, 2H, J=8 Hz), 2.92–2.96 (m, 2H), 3.91 (s, 1H), 7.71 (s, 1H), 10.46 (s, 1H), 11.6–12.4 (br, 2H).

EXAMPLE 24

4-(4,5-DIHYDROXY-6-FORMYL-2-NITROPHENYL)BUTANOIC ACID

The product of the previous example (0.2 g) was demethylated with boron tribromide as described in example 10. The product was purified by preparative chromatography using toluene-ethyl acetate-acetic acid 5:2:2 as the eluent. Yield: 20 mg. Mp. 164–168° C.

$^1$H-NMR (DMSO-d6, 400 MHz): 1.78–1.82 (m, 2H), 2.32 (t, 2H, J=8Hz), 2.94–2.98 (m, 2H), 7.53 (s, 1H), 10.45 (s, 1H), 10.6–12.4 (br, 3H).

What is claimed is:

1. A compound of formula I

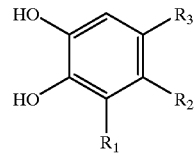

wherein $R_1$ is nitro, cyano, formyl or carboxy;

$R_2$ is —A—$R_4$, wherein
A is a branched or straight chain $C_{1-9}$ alkylene and
$R_4$ is carboxy or 5-tetrazolyl;

$R_3$ is nitro, cyano, halogen, formyl, carboxy, $C_{1-5}$ alkyl carbonyl, aryl carbonyl or $SO_2R_6$, wherein
$R_6$ is a branched or straight chain $C_{1-5}$ alkyl, aryl alkyl, aryl or $NR_7R_8$, wherein
$R_7$ and $R_8$ are independently hydrogen, a branched or straight chain $C_{1-5}$ alkyl or together form a $C_{3-6}$ ring;
or a pharmaceutically acceptable ester or salt thereof.

2. The compound according to claim 1, wherein $R_1$ and $R_3$ are both nitro.

3. The compound according to claim 1, wherein $R_1$ and $R_3$ are both cyano.

4. The compound according to claim 1, wherein A has at least two carbon atoms.

5. The compound according to claim 2, wherein A has at least two carbon atoms.

6. The compound according to claim 3, wherein A has at least two carbon atoms.

7. A method for inhibiting catechol-O-methyl transferase, wherein the method comprises administering to a subject in need of such inhibition an effective amount of a compound of claim 1.

8. A pharmaceutical composition comprising the compound of claim 1 or an ester or a salt thereof and a pharmaceutically acceptable carrier.

9. A method for the treatment of Parkinson's disease or hypertension comprising administering to a subject in need of such treatment an effective amount of the compound of claim 1 or an ester or a salt thereof.

* * * * *